United States Patent [19]

Decupper

[11] Patent Number: 5,434,419
[45] Date of Patent: Jul. 18, 1995

[54] PROCESS AND DEVICE FOR MONITORING APPARATUS FOR EMISSION OF ELECTRO-MAGNETIC RADIATIONS

[76] Inventor: Jean Decupper, Les Sous-Bois de Sansovino, 39 Chemin de Caldana, 06400 Cannes, France

[21] Appl. No.: 167,364

[22] Filed: Dec. 16, 1993

[30] Foreign Application Priority Data

Dec. 22, 1992 [FR] France ................... 92 15486

[51] Int. Cl.$^6$ .................................................. G01J 3/02
[52] U.S. Cl. .................................. 250/372; 250/492.1
[58] Field of Search ................ 250/372, 373, 372 EM, 250/492.1, 436, 432 R

[56] References Cited

U.S. PATENT DOCUMENTS

| | | | |
|---|---|---|---|
| 3,427,489 | 2/1969 | Walsh III | 313/101 |
| 3,629,587 | 12/1971 | Decupper . | |
| 4,061,922 | 12/1977 | Last | 250/461 |
| 4,103,167 | 7/1978 | Ellner | 250/372 |
| 4,659,930 | 4/1987 | Johnson et al. | 260/336.1 |
| 4,885,471 | 12/1989 | Telfair et al. | 250/461.1 |
| 5,115,138 | 5/1992 | Tanaka et al. | 250/372 |

FOREIGN PATENT DOCUMENTS

| | | |
|---|---|---|
| 0392442 | 10/1990 | European Pat. Off. . |
| 2639433 | 5/1990 | France . |
| 62-54129 | 3/1987 | Japan . |
| 2122130 | 6/1987 | Japan ................. 250/372 |
| 2137527 | 6/1987 | Japan ................. 250/372 |

*Primary Examiner*—Paul M. Dzierzynski
*Assistant Examiner*—Richard Hanig
*Attorney, Agent, or Firm*—Fisher, Christen & Sabol

[57] ABSTRACT

The invention relates to a process for monitoring the flowrate and intensity of an electro-magnetic emission, particularly of very short wave-length, in the vicinity of visible light, such as a wave emission in the ultra-violet, for germicidal or bacteriostatic or atmosphere purifying purposes, characterized in that a first and a second sensor are exposed to the radiations to be monitored, each sensor constituted by a transducer, particularly of the photovoltaic type, while a series of filters is interposed in front of said sensors, such that a first sensor is rendered exclusively sensitive to the radiations of the wave-length to be monitored, while the second sensor is rendered insensitive to said radiations, the currents issued by each of these transducers are permanently compared, the differential between the two currents being proportional to the intensity of the radiation monitored, which makes it possible to display this intensity. The invention also relates to a device for carrying out this process.

18 Claims, 3 Drawing Sheets

PROCESS AND DEVICE FOR MONITORING APPARATUS FOR EMISSION OF ELECTRO-MAGNETIC RADIATIONS

FIELD OF THE INVENTION

The present invention relates to a process and device for detecting and monitoring the intensity of an electromagnetic emission of very short wave-length, lying in the vicinity of visible light, such as wave emissions in the ultra-violet for germicidal, atmosphere purifying purposes.

Although the invention is described hereinafter in connection with a more specific, more particular application, namely the monitoring of tubes for emission of germicidal ultra-violet radiations, it is more generally applicable to the monitoring of apparatus for emission of electro-magnetic radiations lying in particular in the vicinity of visible light.

The more specific application which is considered herein concerns a control in order to alert the service staff immediately when a germicidal apparatus, emitting ultra-violet radiations, falls below a minimum efficiency threshold.

BACKGROUND OF THE INVENTION

Such apparatus constituted by a fluorescent electric tube emitting radiations in the ultra-violet, of a very precise wave-length, are known to be used in particular in sensitive environments at risk, such as medical or hospital premises, rooms for preservation, working or packing food products, etc.

The ultra-violet radiations of the known wave-length (2537 Angströms) are used for their specifically germicidal and bacteriostatic properties.

To that end, boxes containing the radiation emitter tubes are used (avoiding these radiations attaining the staff's sight), the air being capable of being placed in natural or forced circulation around the tubes so as to provoke, as such circulation continues, the destruction of the germs present on the micro-dust in suspension in the air.

It is also known that such U.V. radiation generator tubes are subjected to ageing when their radiation intensity and flowrate drop, in the same way as, further to deposits, dirt or dust, they may lose a large part of their efficiency.

As these tubes emit, parallel to the ultra-violet radiations, radiations in the visible light, particularly blue, it is not possible to detect, a priori and simply by looking, the state of functioning or the degree of efficiency of the radiation, since only the blue light visible to the eye may be detected and this light, totally inefficient and without germicidal properties per se, is in no way a sign of the existence and magnitude of the parallel ultra-violet emissions.

Consequently, the U.V. tube frequently remains in place, continuing to emit its bluish light, whilst it has become totally inefficient without any germicidal action.

In the present state of the art, in order to detect the state of non-functioning of an U.V. tube further to ageing thereof or to deposit of dirt forming a screen, these tubes must be subjected to periodic maintenance in the form of an individual examination to check, during this systematic operation, the apparatus having to be replaced, renovated or maintained.

Consequently, the efficient maintenance of these apparatus depends on the staff's vigilance and any shortcoming in this respect leads to consequences which may be fatal for the patients, if only because, between two spot checks, one or more tubes may have become totally inefficient, which inefficiency will possibly be detected only at the subsequent control, consequently leaving a period of time during which the air is not protected.

In addition, verification is effected by using a portable dosimeter which requires opening the housing of the apparatus, the U.V. tubes necessarily being in action at that moment; the dosimeter is exposed to the field of the radiations emitted by the tube for a determined time, period during which the service staff therefore remains exposed to the U.V. radiations; such working conditions are not satisfactory as they are dangerous for the operator's sight and face; for these reasons, hospital staff have no great incentive to carry out such periodic verifications.

There is therefore a need for a method and apparatus making it possible to avoid, on the one hand, leaving an apparatus apparently in operation whilst it is in fact inactive, and, on the other hand, exposing the service staff to the U.V. radiations when making the verifications.

It is precisely an object of the invention to respond to this need and to overcome the drawbacks and shortcomings of the prior art as set forth hereinbefore.

SUMMARY OF THE INVENTION

To that end, the invention relates to a process for monitoring the intensity of an electro-magnetic emission of very short wave-length, in the vicinity of visible light, such as wave emissions in the ultra-violet, for germicidal and bacteriostatic or atmosphere purifying purposes, said process being characterized in that a first and a second sensor are exposed to the radiations to be monitored, each sensor constituted by a transducer, particularly of the photovoltaic type, whilst a series of filters is interposed in front of said sensors, such that a first sensor is rendered exclusively sensitive to the radiations of the wave-length to be monitored, whilst the second sensor is rendered insensitive to said radiations, the currents issued by each of these transducers are permanently compared, the differential between the two currents being proportional to the intensity of the radiation monitored, which makes it possible to display this intensity.

According to a development of the process, a minimum reference threshold of said differential is determined, below which is actuated a visual or sound alarm means or a relay triggering off an automatic intervention such as the cut-off of supply of the emitter being monitored.

According to a development of the process, there are interposed in front of the photovoltaic transducers a first filter and a second filter adapted to attenuate or stop the adjacent marginal radiations lying in the visible light and a second filter adapted to transform the emission of radiations monitored into visible light adapted to be detected by a transducer of the photoelectric cell type.

In accordance with a development of the above process, the emissions are permanently monitored so that any failure due to ageing or for any other reason, may be immediately detected and indicated when it has attained a predetermined level.

The invention also relates to a device for carrying out the above process, for permanently detecting, controlling and monitoring an emitter of electro-magnetic radiations of wave-length located in the ultra-violet and particularly for germicidal and atmosphere purifying purposes, more especially in sensitive environments such as medical premises, hospitals or premises where food products are treated, said device being characterized in that it comprises two identical photoelectric cells disposed in the field of the radiation monitored, a plurality of filters being interposed in said field between the emitter and the cells and the filters being such that a first cell is rendered sensitive to only the radiations of the wave-length monitored, whilst a second cell is rendered insensitive to said radiations, the voltaic currents issued by the two photoelectric cells being of different intensity by reason of this difference, and this for normal functioning of the emitter, and the two voltaic currents being collected at the terminals of a comparator programmed to tip a relay when the differential between the two currents falls below a determined reference value.

According to a feature of the invention, the control and monitoring device comprises a relay adapted to cut off the supply of the emitter and, in parallel, to actuate a signalling assembly.

According to another feature, the monitoring device comprises a first filter or group of filters adapted to attenuate or stop the marginal radiations adjacent the wave-length monitored and lying in the visible light spectrum, and it comprises a second filter adapted to transform the emission of the radiation to be monitored into visible light adapted to be detected by the photoelectric cells, whilst the second photoelectric cell comprises alone a filter occulting the visible radiation resulting from said transformation, the visible radiation resulting from this transformation being received only by the first cell.

The monitoring device is preferably permanently associated with an ultra-violet emitter itself constituted by an ultraviolet emission tube integrated in a protective housing.

According to a variant, the device is permanently mounted in the immediate proximity of the emitter of radiations to be monitored and at least the photo-electric cells comprise means ensuring their displacement from a retracted position towards an active position in which they are located in the field of the radiation to be monitored.

According to a more particular embodiment, the apparatus comprises an assembly of components mounted on a base which is itself magnetic, enabling it to be positioned on the metal housing of the box of an U.V. radiation emission apparatus.

The monitoring apparatus advantageously comprises a split shaft potentiometer for adjusting the threshold of sensitivity, i.e. the intensity of radiations below which the intensity of the radiations is considered as insufficient and inefficient.

The monitoring apparatus advantageously comprises a relay adapted to cut off its own supply when the emission subjected to monitoring falls below the determined reference threshold, the apparatus being mounted in series upstream of the emitter apparatus, cut-off of the supply consequently stopping the emitter apparatus itself.

According to a variant embodiment, the apparatus comprises an assembly bearing electronic components, connections, alarm means and protection means grouped on a base comprising a magnetic sole allowing positioning on the metal housing of the U.V. emission apparatus, and the base is associated with a separate box connected to said base by a wire linkage, the box comprising the two cells and the filters, adapted to be positioned in the field of the U.V. radiations, this box also comprising a sole which is magnetic for fixation thereof.

Finally, according to a variant embodiment, each monitoring apparatus is connected by a signalling circuit to a central control and monitoring console grouping the signals coming from all the U.V. apparatus belonging to the same unit.

BRIEF DESCRIPTION OF THE DRAWINGS

The invention will be more readily understood on reading the following description with reference to the accompanying drawings, in which.

DETAILED DESCRIPTION OF THE DRAWINGS

Figure 1:
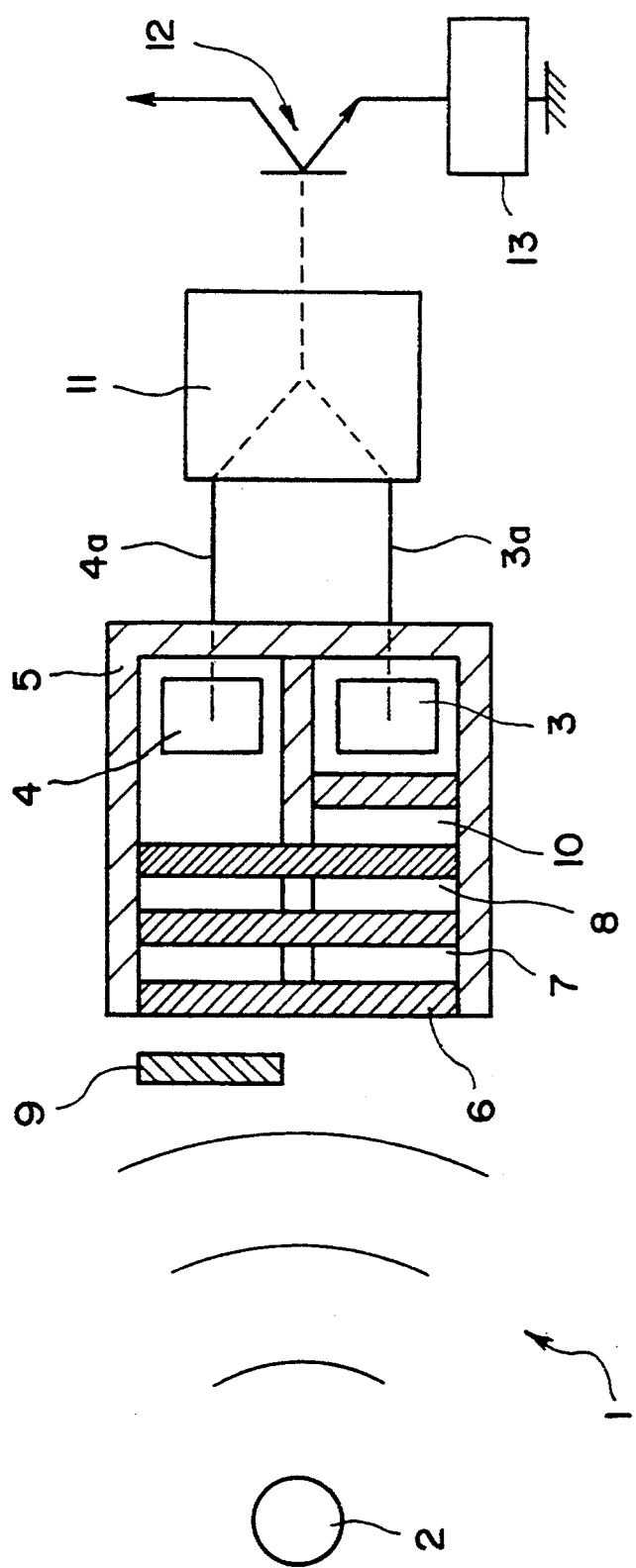
FIG. 1 is a schematic view of the means employed within the framework of the present invention.
Figure 2:
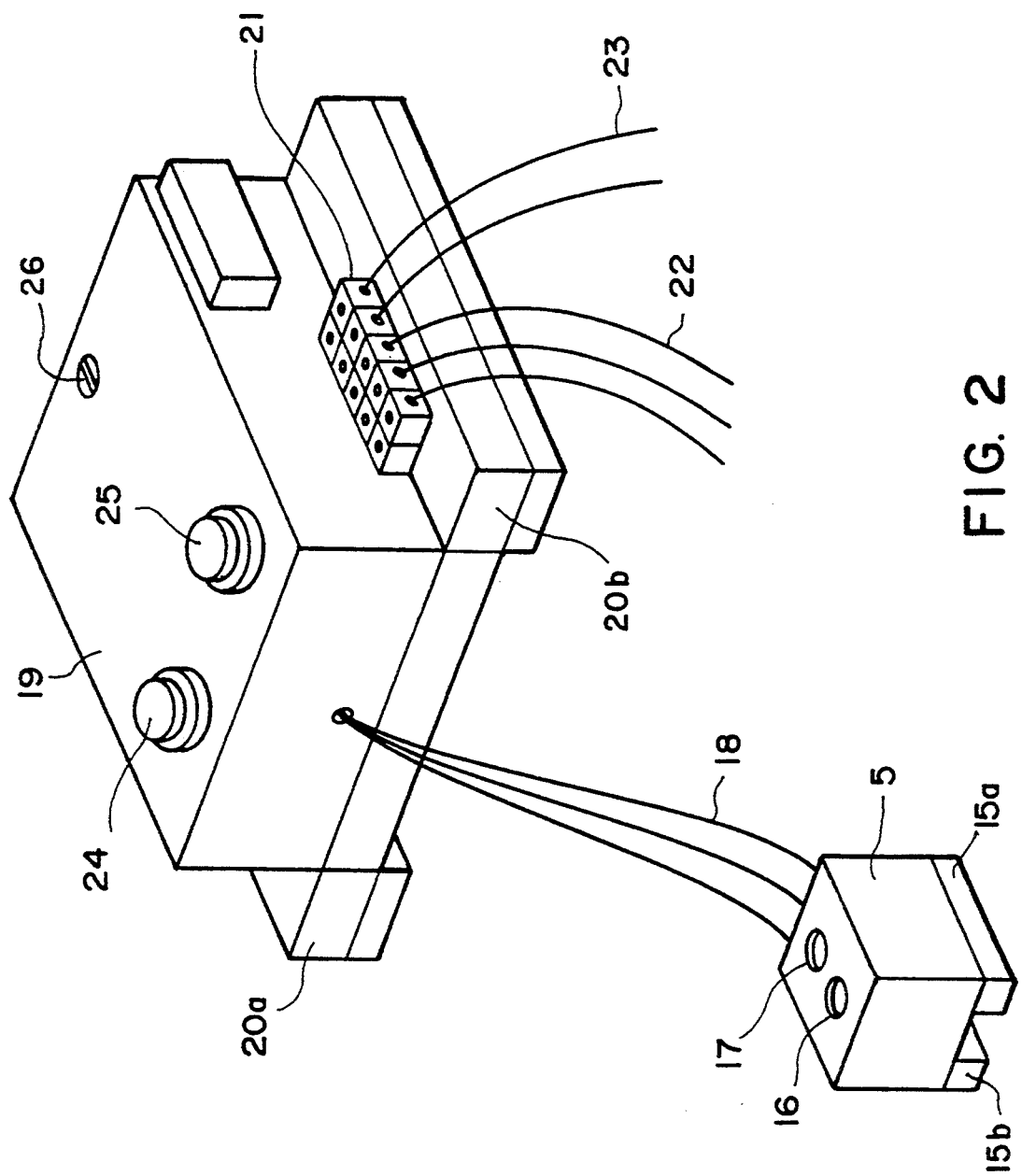
FIG. 2 is a schematic view in perspective of an embodiment of the monitoring apparatus according to the invention.

Referring now to the drawings, FIGS. 1 and 2 firstly schematically show a radiation emitter in the form of an U.V. tube, of known type.

This U.V. tube is itself inserted in a housing and systematically positioned in premises with sensitive environment, such as medical premises, hospitals, public premises, sanitary premises, kitchens, workshops for preparing and packing food products or the like.

Figure 3:
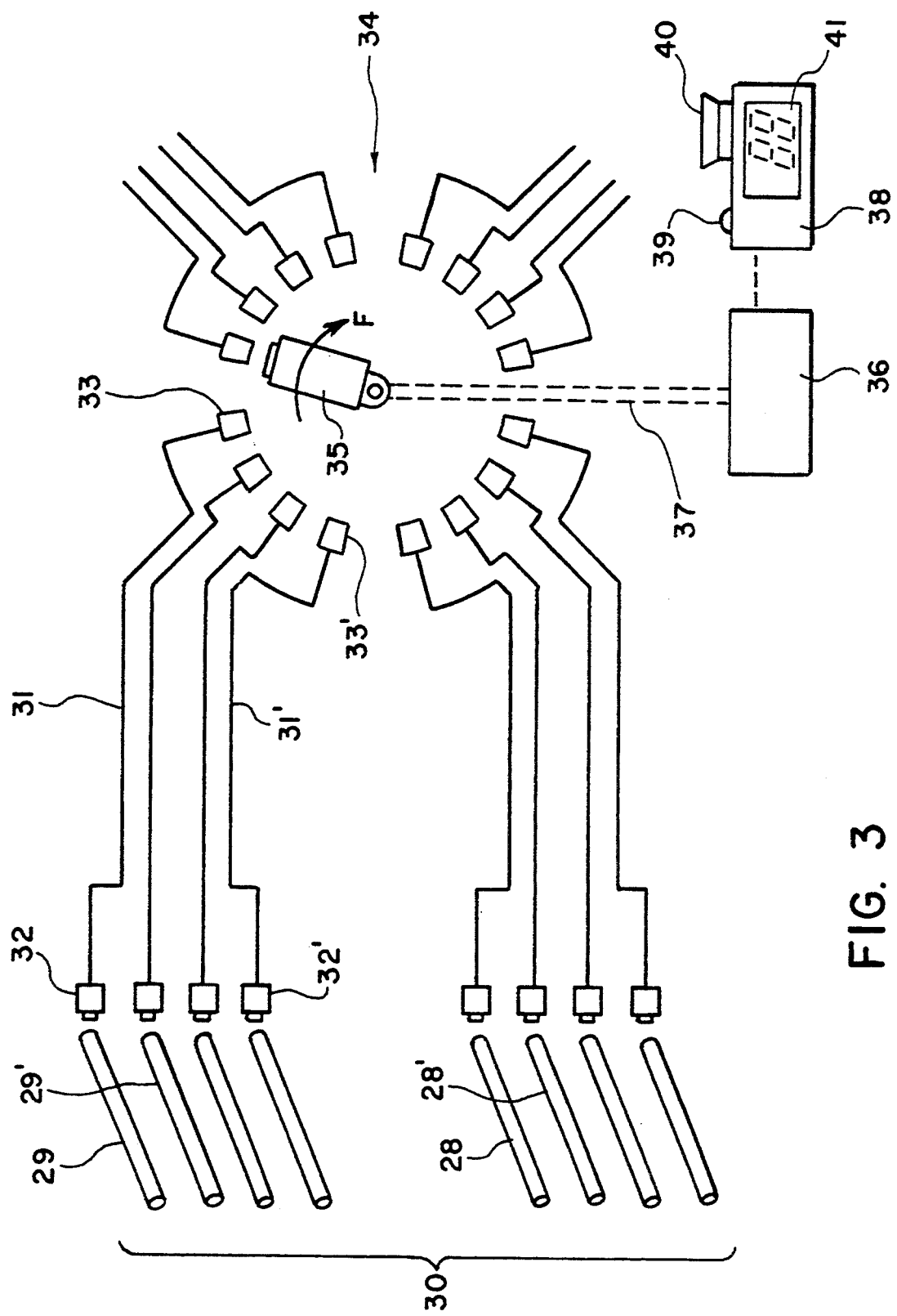
FIG. 3 shows a system for monitoring a bank of tubes.

It will be understood that the major difficulty within the framework of the problem set forth here, consists in eliminating the influence of the lights of adjacent wave-length in the visible spectrum and in particular of the bluish light which is permanently emitted by the tube, and this independently of its efficiency as to the emission of the ultra-violet radiation effective for its bactericidal action; FIG. 3 illustrates a variant of the device according to the invention adapted for the simultaneous, combined monitoring of a plurality of radiation emitter tubes disposed in a bank.

Within the framework of the invention, two physically and electronically identical photoelectric cells, namely the first photoelectric cell 3 and the second photoelectric cell 4 twinned and capable of being mounted in a common box 5, are exposed to the radiations of tube 2.

These cells are exposed so as to receive the radiations 1 coming from tuba 2.

However, there are interposed in front of the cells a plurality of first light modifying means 6, 7, 8 intended to stop, in order to eliminate the parasitic effect therefrom, the radiations lying in the visible light, whilst one of these light modifying means is a down-conversion means which is provided to transform the ultra-violet radiations into visible light, particularly green light and the other two are filters.

In addition, the filtering plate 9 interposed in front of the second photoelectric cell 4 stops the radiations lying in the wave-length monitored, i.e. the ultra-violet radiations.

Consequently, the first cell 3 is rendered sensitive to the ultra-violet radiations, i.e. to the visible green light resulting from the transformation of the ultra-violet radiations into green light.

The second cell 4 is itself insensitive to the ultra-violet radiations which cannot attain it, having been filtered at the level of the filtering plate 9.

The two photoelectric cells 3 and 4 are, in addition, rendered insensitive to the visible light, which is eliminated by the filters interposed upstream.

In addition, there may be added to this filtering assembly the filtering plate 10 located upstream of the first cell 3, this fourth source of filtration being rendered transparent to only the green light resulting from the transformation of the ultra-violet radiations.

The two cells 3 and 4 deliver a voltaic current which results from the transformation of the light energies received into electric energy.

These two currents are transmitted to an integrated circuit 11, which performs the role of comparator.

It will be understood that the two twinned cells 3 and 4 deliver a necessarily different current, at least during the normal period of emission of the tube 3 since one cell receives, in the form of green visible light, the energy coming from the ultra-violet radiations, whilst this energy is eliminated at the level of the second cell 4.

The difference or the differential between the two currents coming from cells 3 and 4 and transmitted by circuits 3a and 4a may be detected and analyzed at the level of the comparator 11.

The higher the differential, the more the electro-magnetic radiation monitored may be considered as satisfactory.

When the electro-magnetic radiation monitored, for example the ultra-violet radiation, disappears, the first photoelectric cell 3 does not receive more energy than the control cell 4; it may be considered that this absence of differential consequently translates the inexistence of ultra-violet radiations emitted by the tube.

It is thus convenient to display a reference value at this differential, reference value below which the emission of U.V. radiations is considered as unsatisfactory and inacceptable.

The transistor 12 is then tipped to actuate a relay 13.

This relay may be of any suitable type and may correspond to the activation of a visual or sound signalling apparatus; this may be an acoustic device 14 as shown in FIG. 2.

The relay 13 may transmit any alarm signal, particularly to a central console from a monitoring room.

According to a variant, the relay 13 is inserted on the supply of the apparatus itself; the monitoring apparatus being mounted in series and upstream of the radiation emission apparatus, particularly of the supply of the U.V. tube, with the result that the apparatus cuts off its own supply, consequently interrupting the supply of the U.V. tube.

It will already be noted that, in this case, signalling is thus automatically effected since the extinction of the U.V. tube causing the bluish visible light to disappear indicates to the service staff the inactive position of the tube further to its failure as U.V. radiation emitter.

FIG. 2 shows in perspective an assembly according to the invention comprising, on the one hand, a box 5 mounted on a magnetic sole or double magnetic sole 15a, 15b enabling the box to be fixed simply without boring inside the housing of an U.V. radiation emitter apparatus, the openings 16 and 17 being exposed facing the U.V. tube to allow reception of the radiations by the photoelectric cells 3 and 4 disposed inside the box 5.

The wire link 18 corresponding to the circuits 3a and 4a terminates at the base 19 itself mounted on the magnetic soles 20a and 20b allowing its fixation inside or outside the housing of the U.V. emitter apparatus.

Terminal 21 allows the connection for reception of the supply from mains 22 and the departure of supply 23 towards the U.V. tubes.

The manual contactor 24 in the form of a push button makes it possible to stop the acoustic device and possibly to re-set the apparatus after the alarm has been given; a protecting fuse 25 is also positioned on the box.

The potentiometer located inside the base 19 may be actuated and adjusted by its split shaft output 26 of known type.

The invention therefore makes it possible to produce, with economic means, an assembly for permanently monitoring U.V. tubes placed in a sensitive medium subjected to the action of germicidal radiations.

Such monitoring avoids concern, from a social and medical standpoint, since the apparatus is automatically de-activated as soon it has ceased being efficient, signalling its state to the staff, itself; normally, a tube having ceased to be efficient will be rapidly located and replaced without the staff being exposed to the radiations or having to make a routine intervention which would represent a loss of time insofar as the majority of apparatus are in a good state.

Improved working conditions, a greater efficiency in bacteriostatic monitoring of the environment, and a saving in manpower are thus attained in a hospital or in food-producing premises.

This application may be particularly employed in the case of a bank of joined tubes intended to ensure purification and sterilization of a fluid passing through the emission zone.

The invention may also be applied to tubes emitting ultra-violet radiations disposed to act on a flow or a circuit of water inserted in a swimming pool filtering and purifying assembly.

It will be understood that, in any case, it is not possible to decentralize monitoring at the level of each tube, the latter being disposed in a zone which, in principle, is of difficult access.

It is therefore necessary in that case to offset signalling and possibly detection with respect to the apparatus monitored.

It is therefore necessary in that case to dispose in the vicinity of the tube a probe for receiving the radiations and to transport these latter by an appropriate network to a central station from which the waves or data may be processed with a view to locating the deflections and to triggering off an alarm.

FIG. 3 shows a variant of the device for remotely controlling a plurality of tubes emitting radiations of a determined wave-length and in which each emitter tube is connected to a central monitoring station by a wave guide, particularly an optical fiber cable known per se and specific to each tube, a distal end of the wave guide being adapted to receive the radiation from a determined tube, whilst a proximal end of the wave-guide is adapted to deliver this radiation to a central monitoring station, this latter thus being adapted to receive part of the radiations emitted by each tube and transmitted by said wave-guide, the central station further comprising a double photoelectric cell in accordance with the above characteristics, and it is provided, in addition, with mechanical means for positioning the double cell in interrogation position successively in front of each of the proximal ends of the wave-guide.

FIG. 3 shows that tubes 29, 29', 28, 28' are grouped together to constitute a bank 30.

Each tube is associated with a wave-guide 31, 31' comprising a distal end 32, 32' disposed facing each of the tubes that this guide serves.

The opposite end 33, 33' of this wave-guide is located at the level of the central station 34.

Under these conditions, each wave guide 31 picks up an emission at its distal or inlet end 32, located in the proximity of a particular tube and this radiation is re-emitted at the proximal end 33' within the central station 34.

The distal ends of all the wave guides are disposed for example in a circle in the present case.

An assembly of twinned cells 35 is mounted on a rotating arm disposed radially at the centre of the ring formed by the proximal ends of the wave guides.

This assembly of twinned cells 35 is associated with mechanical means, for example an electric motor which drives it in angular rotation in a step-by-step movement represented in FIG. 3 by arrow F.

Under these conditions, it is seen that the assembly of cells 35 may be placed in interrogation position successively facing each of the proximal ends of one of the wave guides corresponding to a tube.

At each of these control interrogations, the photoelectric cell is adapted to capture the radiations and to transform them to give voltaic comparison currents in accordance with what was described hereinbefore.

These voltaic currents are transmitted to a comparator 36 by circuits 37 and trigger off an alarm as described previously in the case of the distorsion between the two signals falling below a certain threshold.

The alarm signal is transmitted to unit 38, which is provided with a luminous signalling means 39 possibly with an acoustic device 40 and a display assembly 41 signalling by a mark that apparatus whose insufficiency has been detected.

It will be understood that this variant which enables banked tubes to be monitored, may be replaced by a system in which a double cell is positioned at the level of each tube; the voltaic currents collected at the output terminals of the twinned cells are sent to the central station to be processed therein, the central station being adapted successively to compare the output currents of each assembly of twinned cells in order, in the case of difference falling below a determined threshold, likewise to trigger off an alarm.

The invention therefore makes it possible, by this development, to monitor in decentralized manner tubes grouped in a technical assembly of difficult access which would render local monitoring operations delicate.

Access to the zone may thus be limited to the very precise case of the alarm having detected the insufficient action of the tube and the latter having to be replaced.

The assembly of photovoltaic transducers 35 is advantageously connected to a comparator adapted to compare the voltages collected at the output terminals of said photovoltaic transducers and to trigger off a signal characterizing the insufficient efficiency of a tube in the wave guide 31 and located, by its proximal end 33 in position of interrogation in front of the assembly 35 of photovoltaic transducers.

What is claimed is:

1. A process for monitoring the flowrate and intensity of an electro-magnetic emission, particularly of very short wave-length, in the vicinity of visible light, such as a wave emission in the ultra-violet, and of the type in which a first and a second sensor are exposed to the radiations to be monitored, the first sensor being a first photovoltaic transducer and the second sensor being a second photovoltaic transducer, while a series of filters is interposed in front of said sensors, such that a first sensor is rendered exclusively sensitive to the radiations of the wave-length to be monitored, while the second sensor is rendered insensitive to said radiations, the currents issued by each of these transducers are compared, the differential between the two currents being proportional to the intensity of the radiation monitored, which makes it possible to display this intensity, wherein, the emission of waves being employed for germicidal or bacteriostatic or atmosphere purifying means, a minimum reference threshold of said differential is determined, below which is actuated a visual or sound alarm means or a relay triggering off an automatic intervention such as the cut-off of supply to the electro-magnetic emission.

2. The process of claim 1, wherein there is interposed in front of the second photovoltaic transducer a first filter adapted to attenuate or stop the adjacent marginal radiations lying in the visible light and there is interposed in front of the other first photovoltaic transducer a second filter adapted to transform the emission of radiations monitored into visible light adapted to be detected by a transducer of the photoelectric cell type.

3. A device for detecting, controlling and monitoring an emitter of electro-magnetic radiations, of the type comprising two sensors, a series of filters sensitive to the radiations to be monitored, a down-conversion means, and means for measuring and comparing between the currents issued by the sensors, wherein said device is arranged to carry out the process of claim 1.

4. A device for detecting, controlling and monitoring an emitter of electro-magnetic radiations, of the type comprising two sensors, a series of filters sensitive to the radiations to be monitored, and means for measuring and comparing between the currents issued by the sensors, wherein said device is arranged to carry out the process of claim 2.

5. A device for permanently detecting, controlling and monitoring an emitter of electro-magnetic radiations of wave-length located in the vicinity of visible light, particularly in the ultra-violet and used for especially for germicidal and atmosphere purifying purposes, more particularly in sensitive environments such as medical premises, hospitals or premises where food products are treated, air-conditioning installations or swimming pools, wherein said device comprises two identical photoelectric cells disposed in the field of the radiation monitored, a plurality of filters being interposed in front of the cells and the filters being such that a first cell is rendered sensitive to only the radiations of the wave-length monitored, whilst a second cell is rendered insensitive to said radiations, the voltaic currents issued by the two photoelectric cells being of different intensity by reason of this difference, and this for a normal period of emission of the emitter, and the two voltaic currents being collected at the terminals of a comparator programmed to tip a relay when the differential between the two currents falls below a determined reference value.

6. The control and monitoring device of claim 5, wherein it comprises a relay adapted to cut off the supply of the emitter and, in parallel, to actuate a signalling assembly.

7. The monitoring device of claim 5, wherein it comprises a first filter or group of filters adapted to attenuate or stop the marginal radiations adjacent the wavelength monitored and lying in the visible light spectrum, and it comprises a down-conversion means adapted to transform the emission of the radiation to be monitored into visible light adapted to be detected by the first photoelectric cell, whilst the second photoelectric cell comprises alone a filter occulting the visible radiation resulting from said transformation, the visible radiation resulting from this transformation being received only by the first cell.

8. The device of claim 5, wherein it is permanently associated with an ultra-violet emitter itself constituted by an ultraviolet emission tube integrated in a protective housing.

9. The device of claim 8, wherein it is permanently mounted in the immediate proximity of the emitter of radiations to be monitored, whilst at least the photoelectric cells comprise means ensuring their displacement from a retracted position towards an active position in which they are located in the field of the radiation to be monitored.

10. The device of claim 5, wherein it comprises an assembly of components mounted on a base which is itself magnetic, enabling it to be positioned on the metal housing of the box of an U.V. radiation emission apparatus.

11. The device of claim 5, wherein it comprises a split shaft potentiometer for adjusting the threshold of sensitivity, i.e. the intensity of radiations below which the intensity of the radiations is considered as insufficient and inefficient.

12. The device of claim 5, wherein it comprises a relay adapted to cut off its own supply when the emission subjected to monitoring falls below the determined reference threshold, the apparatus being mounted in series upstream of the emitter apparatus, cut-off of the supply consequently stopping the emitter apparatus itself.

13. The device of claim 5, wherein it comprises an assembly bearing electronic components, connections, alarm means and protection means grouped on a base comprising a magnetic sole allowing positioning on the metal housing of the U.V. emission apparatus, and the base is associated with a separate box connected to said base by a wire linkage, the box comprising the two cells and the filters, adapted to be positioned in the field of the U.V. radiations, this box also comprising a sole which is magnetic for fixation thereof.

14. The device of claim 5, wherein it is connected by a signalling circuit to a central control and monitoring console grouping the signals coming from all the U.V. apparatus belonging to the same unit.

15. The device of claim 5, wherein the assembly of filters and cells is disposed in the field radiated by the ultra-violet emitter, inside the apparatus but not in direct contact with the U.V. tube so as to avoid the rapid destruction of the cells.

16. A device for remote-controlling a plurality of U.V. radiation emitter tubes, disposed in a bank, wherein each emitter tube belonging to said bank is connected to a central monitoring station by a wave guide, particularly in optical fiber form, each guide being specific to a tube and comprising a distal end facing said tube and a proximal end adapted to deliver the radiation transmitted to the level of the central station, this latter thus being adapted to receive the radiations emitted and transmitted by said wave guides by each of the tubes, and the central station is provided with an assembly of photovoltaic transducers, particularly photoelectric cells, provided with a first set of light modifying means intended to stop the radiations lying in the visible light, one light modifying means of said first set being provided to transform the ultra-violet radiations into visible light, particularly green light, and a second set of filters adapted to stop the radiations lying in the wave-length monitored, i.e., the ultra-violet radiations, and a third set of filters being rendered transparent to only the green light resulting from the transformation of the ultra-violet radiations, the central station comprising mechanical means, particularly an electric motor adapted to position said assembly of photovoltaic transducers successively facing the proximal end of each of the wave guides, each time allowing the supply of said transducers with radiation coming successively from each of the tubes.

17. The device of claim 16, wherein the proximal ends of the wave guides are disposed along a line parallel to the path of the input of the photovoltaic transducer assembly, and in particular said proximal ends of the wave guides are disposed in a circle, the assembly of photovoltaic transducers being disposed in radial position and being animated by a step-by-step angular movement allowing it to come successively into position of interrogation in front of each of said proximal ends of the wave guides.

18. The device of claim 16, wherein each tube comprises an assembly of twinned photovoltaic transducers and each assembly is connected to a central station by an appropriate circuit specific to the corresponding tubes, the central station being adapted to compare the characteristics of the voltages collected at the output of said photovoltaic transducer assemblies to deduce therefrom the state of functioning of the corresponding tubes.

* * * * *